United States Patent [19]

Heider et al.

[11] Patent Number: 4,871,735

[45] Date of Patent: Oct. 3, 1989

[54] NAPHTHYL DERIVATIVES, PHARMACEUTICAL COMPOSITIONS CONTAINING THESE COMPOUNDS AND PROCESSES FOR PREPARING THEM

[75] Inventors: Joachim Heider, Warthausen; Manfred Psiorz; Andreas Bomhard, both of Biberach; Norbert Hauel, Biberach-Bachlangen; Berthold Narr, Biberach; Klaus Noll, Warthausen, all of Fed. Rep. of Germany; Christian Lillie; Walter Kobinger, both of Vienna, all of Fed. Rep. of Germany; Jurgen Dammgen, Sulmingen, Austria

[73] Assignee: Dr. Karl Thomae GmbH, Biberach an der Riss

[21] Appl. No.: 96,097

[22] Filed: Sep. 11, 1987

[30] Foreign Application Priority Data

Sep. 12, 1986 [DE] Fed. Rep. of Germany ....... 3631013

[51] Int. Cl.$^4$ .................... A61K 31/55; C07D 222/16
[52] U.S. Cl. .................... 514/213; 514/291; 514/307; 514/309; 514/411; 514/416; 514/217; 540/522; 540/523; 540/594; 540/586; 546/90; 546/141; 546/145; 548/472; 548/429
[58] Field of Search ............... 540/523, 594, 522, 586; 546/141, 145, 90; 548/472, 429; 514/213, 307, 309, 416, 411, 217, 291

[56] References Cited

U.S. PATENT DOCUMENTS

| 4,137,318 | 1/1979 | Eberlein et al. | 540/523 |
| 4,490,369 | 12/1984 | Reiffen et al. | 540/523 |
| 4,584,293 | 4/1986 | Reiffen et al. | 540/594 |
| 4,616,011 | 10/1986 | Reiffen et al. | 540/523 |

FOREIGN PATENT DOCUMENTS

| 224318 | 7/1985 | German Democratic Rep. | 546/145 |
| 622781 | 4/1981 | Switzerland | 546/140 |
| 1548844 | 7/1979 | United Kingdom | 541/141 |

Primary Examiner—Robert T. Bond

Attorney, Agent, or Firm—David E. Frankhouser; Alan R. Stempel; Mary-Ellen M. Timbers

[57] ABSTRACT

The present invention relates to new naphthyl derivatives of general formula

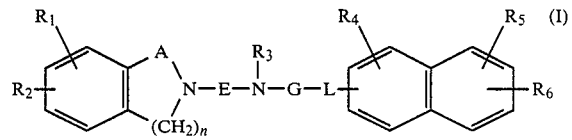

wherein N represents the number 1 or 2, A represents a —CH$_2$—, —CO—, —CH$_2$CH$_2$—, —CH=CH—,

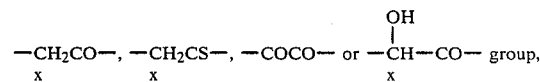

while the atom marked with an x is linked to the phenyl nucleus, E represents a straight chained alkylene group optionally substituted by an alkyl group, G represents a straight chained alkylene group optionally substituted by an alkyl group, L represents a bond or an oxygen atom, if G represents a straight chained alkylene group with 2 to 5 carbon atoms optionally substituted by an alkyl group, R$_1$ and R$_2$, which may be identical or different, represent alkyl or alkoxy groups or R$_1$ and R$_2$ together represent an alkylenedioxy group, R$_3$ represents a hydrogen atom, or an alkyl or an allyl group, R$_4$, R$_5$ and R$_6$, which may be identical or different, represent hydrogen atoms, alkyl or alkoxy groups, the enantiomers and the acid addition salts thereof, which have valuable pharmacological properties, particularly a heart rate lowering activity.

The new compounds may be prepared using methods known per se.

7 Claims, No Drawings

NAPHTHYL DERIVATIVES, PHARMACEUTICAL COMPOSITIONS CONTAINING THESE COMPOUNDS AND PROCESSES FOR PREPARING THEM

British Patent 1 548 844 describes, inter alia, the compound of formula

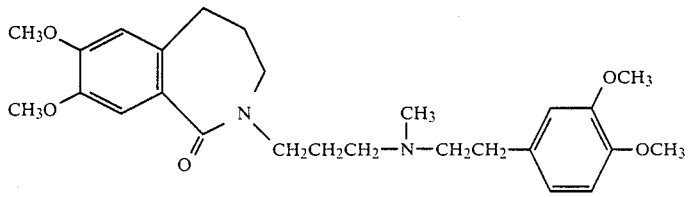

and the physiologically acceptable acid addition salts thereof which have valuable pharmacological properties, namely a mild hypotensive activity and, more particularly, a selective heart rate-lowering activity.

Surprisingly, it has now been found that the new naphthyl derivatives of general formula

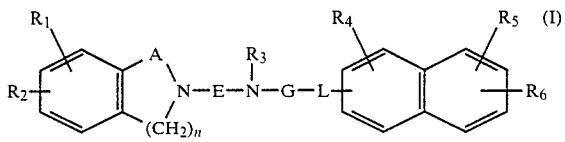

the enantiomers of such compounds if they contain an optically active carbon, and the acid addition salts thereof, particularly the physiologically acceptable acid addition salts with inorganic or organic acids, have even more valuable pharmacological properties, particularly a long-lasting heart rate lowering effect and the effect of reducing the $O_2$ requirements of the heart.

The present invention thus relates to the new naphthyl derivatives of general formula I above, the enantiomers and the acid addition salts thereof, more particularly, for pharmaceutical use, the physiologically acceptable acid addition salts thereof with inorganic or organic acids, processes for preparing them and pharmaceutical compositions containing these compounds.

In general formula I above
n represents the number of 1 or 2,
A represents a $-CH_2-$, $-O-$, $-CH_2CH_2-$, $-CH=CH-$, $$-CH_2CO-, -CH_2CS-, -COCO- \text{ or}$$
$$\phantom{-CH_2}x\phantom{CO-,-CH_2}x$$

$$-CHOH-CO- \text{ group,}$$
$$\phantom{-CHOH-}x$$

wherein the atom marked with an x is linked to the phenyl nucleus,
E represents a straight chained alkylene group with 2 to 4 carbon atoms optionally substituted by an alkyl group with 1 to 3 carbon atoms,
G represents a straight chained alkylene group with 1 to 5 carbon atoms optionally substituted by an alkyl group with 1 to 3 carbon atoms,
L represents a bond or an oxygen atom, if G represents a straight chained alkylene group with 2 to 5 carbon atoms optionally substituted by an alkyl group with 1 to 3 carbon atoms,
$R_1$ and $R_2$, which may be identical or different, represent alkyl or alkoxy groups each having 1 to 3 carbon atoms in each alkyl moiety or $R_1$ and $R_2$ together represent an alkylenedioxy group with 1 or 2 carbon atoms,
$R_3$ represents a hydrogen atom, an akyl group with 1 to 3 carbon atoms or an allyl group,
$R_4$, $R_5$ and $R_6$, which may be identical or different, represent hydrogen atoms, alkyl or alkoxy groups each having 1 to 3 carbon atoms in each alkyl moiety.

As examples of the definitions given for the groups hereinbefore:
A, L and n may be defined as hereinbefore
$R_1$ may represent a methyl, ethyl, n-propyl, isopropyl, methoxy, ethoxy, n-propoxy or isopropoxy group,
$R_2$ may represent a methyl, ethyl, n-propyl, isopropyl, methoxy, ethoxy, n-propoxy or isopropoxy group or together with $R_1$ may represent a methylenedioxy or ethylenedioxy group,
$R_3$ may represent a hydrogen atom, a methyl, ethyl, n-propyl, isopropyl or allyl group,
$R_4$ may represent a hydrogen atom, a methyl, ethyl, n-propyl, isopropyl, methoxy, ethoxy, n-propoxy or isopropoxy group,
$R_5$ may represent a hydrogen atom, a methyl, ethyl, n-propyl, isopropyl, methoxy, ethoxy, n-propoxy or isopropoxy group,
$R_6$ may represent a hydrogen atom, a methyl, ethyl, n-propyl, isopropyl, methoxy, ethoxy, n-propoxy or isopropoxy group,
E may represent an ethylene, n-propylene, n-butylene, 1-methyl-ethylene, 1-ethyl-ethylene, 2-methyl-ethylene, 2-ethyl-ethylene, 1-n-propyl-ethylene, 1-methyl-n-propylene, 2-methyl-n-propylene, 3-methyl-n-propylene, 1-ethyl-n-propylene, 2-n-propyl-n-propylene or 3-ethyl-n-propylene group, and
G may represent a methylene, ethylidene, n-propylidene, n-butylidene, 2-methyl-propylidene, ethylene, 1-methyl-ethylene, 2-ethyl-ethylene, 1-propyl-ethylene, 2-methyl-ethylene, 2-ethyl-ethylene, n-propylene, n-butylene, n-pentylene, 1-methyl-n-propylene, 1-methyl-butylene, 1-methyl-n-pentylene, 1-ethyl-n-propylene, 2-ethyl-n-propylene, 1-methyl-n-butylene, ethyleneoxy, n-propyleneoxy, n-butyleneoxy or n-pentyleneoxy group.

Thus, according to the invention, the following compounds are covered by general formula I above:
2-[N-methyl-N-((2-methyl-naphth-1-yl)-eth-2-yl)-amino-prop-3-yl]-6,7-dimethoxy-1,2,3,4-tetrahydro-isoquinolin-1-one,
2-[N-methyl-N-((naphth-2-yl)-prop-2-yl)-amino-prop-3-yl]-6,7-dimethoxy-1,2,3,4-tetrahydro-isoquinolin-1-one, 2-[N-methyl-N-((5-methyl-6-methoxy-naphth-2-yl)-eth-2-yl)-amino-prop-3-yl]-6,7-dimethoxy-1,2,3,4-tetrahydro-isoquinolin-1-one, 3-[N-methyl-N-((6-methoxy-naphth-2-yl)-eth-2-yl)-amino-prop-3-yl]-7,8-dimethoxy-1,3,4,5-tetrahydro-2H-3-benzazepin-2-one, 2-[N-methyl-N-((naphth-2-oxy)-but-4-yl)-amino-prop-3-yl]-7,8-dimethoxy-1,2,3,4-tetrahydro-isoquinolin-1-one, 2-[N-methyl-N-((2-methyl-naphth-1-yl)-methyl)-amino-prop-3-yl]-6,7-dimethoxy-1,2,3,4-tetrahydro-isoquinolin-1-one, 3-[N-methyl-N-((naphth-1-yl)-eth-2-yl)-amino-prop-3-yl]-7,8-dimethoxy-1,3,4,5-tetrahydro-2H-3-benzazepin-2-one, 3-[N-methyl-N-((naphth-1-yl)-eth-2-yl)-amino-prop-3-yl]-7,8-dimethoxy-1,3,4,5-tetrahydro-2H-3-benzazepine, 2-[N-methyl-N-((6-methoxy-naphth-2-yl)-eth-2-yl)-amino-prop-3-yl]-6,7-methylenedioxy-1,2,3,4-tetrahydro-isoquinolin-1-one, 2-[N-methyl-N-((naphth-1-oxy)-eth-2-yl)-amino-prop-3-yl]-5,6-dimethoxy-phthalimidine, 3-[N-methyl-N-((naphth-2-yl)-eth-2-yl)-amino-prop-3-yl]-6,7-dimethoxy-1,2,3,4-tetrahydro-isoquinolin-1-one, 2-[N-methyl-N-((2-methyl-naphth-1-yl)-eth-2-yl)-prop-3-yl]-6,7-methylenedioxy-1,2,3,4-tetrahydro-isoquinolin-1-one, 2-[N-methyl-N-((naphth-2-yl)-prop-2-yl)-amino-prop-3-yl]-6,7-dimethyl-1,2,3,4-tetrahydro-isoquinolin-1-one.

2-[N-methyl-N-((naphth-2-yl)-eth-2-yl)-amino-prop-3-yl]-6,7-methylenedioxy-1,2,3,4-tetrahydro-isoquinolin-1-one, 2-[N-methyl-N-((naphth-2-yl)-prop-3-yl)-amino-prop-3-yl]-6,7-dimethoxy-1,2,3,4-tetrahydro-isoquinolin-1-one, 2-[N-methyl-N-((naphth-2-yl)-prop-3-yl)-amino-prop-3-yl]-6,7-methylenedioxy-1,2,3,4-tetrahydro-isoquinolin-1-one, 2-[N-methyl-N-((naphth-2-yl)-prop-3-yl)-amino-prop-3-yl]-6,7-dimethyl-1,2,3,4-tetrahydro-isoquinolin-1-one, 2-[N-methyl-N-((5-methyl-6-methoxy-naphth-2-yl)-eth-2-yl)-amino-prop-3-yl]-6,7-methylenedioxy-1,2,3,4-tetrahydroisoquinolin-1-one, 2-[N-methyl-N-((naphth-2-oxy)-but-4-yl)-amino-prop-3-yl]-6,7-methylenedioxy-isoquinolin-1-one, 2-[N-methyl-N-((6-methoxy-naphth-2-yl)-eth-2-yl)-amino-prop-3-yl]-6,7-dimethyl-1,2,3,4-tetrahydro-isoquinolin-1-one, 2-[N-methyl-N-((2-methyl-naphth-1-yl)-methyl)-amino-prop-3-yl]-6,7-dimethyl-1,2,3,4-tetrahydro-isoquinolin-1-one, 3-[N-methyl-N-((6-methoxy-5-methyl-naphth-2-yl)-eth-2-yl)-amino-prop-3-yl]-7,8-dimethoxy-1,3,4,5-tetrahydro-2H]-benzazepin-2-one, 3-[N-methyl-N-((2-methyl-naphth-1-yl)-methyl)-amino-prop-3yl]-7,8-dimethoxy-1,3,4,5-tetrahydro-2H]-benzazepin-2-one, 3-[N-methyl-N-((2-naphth-1-yl)-eth-2-yl)-amino-prop-3-yl]-7,8-dimethoxy-1,3,4,5-tetrahydro-2H-benzazepin-2-one, 3-[N-methyl-N-((naphth-1-yl)-prop-2-yl)-amino-prop-3-yl]-7,8-dimethoxy-1,3,4,5-tetrahydro-2H-3-benzazepin-2-one, 3-[N-methyl-N-((naphth-2-oxy)-but-4-yl)-amino-prop-3-yl]-7,8-dimethoxy-1,3,4,5-tetrahydro-2H-3-benzazepin-2-one, 3-[N-methyl-N-((2-methyl-naphth-1-yl)-eth-2-yl)-amino-prop-3-yl]-7,8-dimethoxy-1,3,4,5-tetrahydro-2H-3-benzazepin-2-one, 3-[N-methyl-N-((naphth-1-yl)-eth-2-yl)-amino-prop-3-yl]-7,8-dimethoxy-1,3-dihydro-2H-3-benzazepine, 3-[N-methyl-N-((naphth-1-yl)-eth-2-yl)-amino-prop-3-yl]-7,8-dimethoxy-1,3,4,5-tetrahydro-2H-3-benzazepin-1,2dione, 3-[N-methyl-N-(naphth-1-yl)-eth-2-yl)-amino-prop-3-yl]-7,8-dimethoxy-1-hydroxy-1,3,4,5-tetrahydro-2H-3-benzazepin-2-one, 2-[N-methyl-N-((naphth-2-yl)-methyl)-amino-prop-3-yl]-5,6-dimethoxy-phthalimidine, 2-[N-methyl-N-((naphth-2-yl-oxy)-but-4-yl)-amino-prop-3-yl]-5,6-dimethoxy-phthalimidine, 2-[N-methyl-N-((naphth-1-yl)-eth-2-yl)-amino-prop-3-yl]-5,6-dimethoxy-phthalimidine, 2-[N-methyl-N-((5-methyl-6-methoxy-naphth-2-yl)-eth-2-yl)-amino-prop-3-yl]-5,6-dimethoxy-phthalimidine, 2-[N-methyl-N-((2-methyl-naphth-1-yl)-methyl)-amino-prop-3-yl]-5,6-dimethoxy-phthalimidine, 3-[N-methyl-N-((naphth-2-yl)-eth-2-yl)-amino-prop-3-yl]-7,8-dimethoxy-1,3,4,5-tetrahydro-2H-3-benzazepin-2-one, 2-[N-methyl-N-((5methyl-6-methoxy-naphth-2-yl)-eth-2-yl)-amino-prop-3-yl]-6,7-dimethoxy-1,2,3,4-tetrahydro-isoquinoline, 2-[N-methyl-N-((2-methyl-naphth-1-yl)-methyl)-amino-prop-3-yl]-6,7-dimethoxy-1,2,3,4-tetrahydro-isoquinoline, 2-[N-methyl-N-((naphth-2-oxy)-but-4-yl)-amino-prop-3-yl]-6,7-dimethoxy-1,2,3,4-tetrahydro-isoquinoline, 2-[N-methyl-N-((naphth-2-yl)-eth-2-yl)-amino-prop-3-yl]-6,7-dimethyl-1,2,3,4-tetrahydro-isoquinolin-1-one.

2-[N-methyl-N-((2-methyl-naphth-1-yl)-eth-2-yl)-amino-prop-3-yl]-6,7-dimethyl-1,2,3,4-tetrahydro-isoquinolin-1-one, 2-[N-methyl-N-((naphth-2-yl)-prop-2-yl)-amino-prop-3-yl]-6,7-methylenedioxy-1,2,3,4-tetrahydro-isoquinolin-1-one, 2-[N-methyl-N-((5-methyl-6-methoxy-naphth-2-yl)-eth-2-yl)-amino-prop-3-yl]-6,7-dimethyl-1,2,3,4-tetrahydro-isoquinolin-1-one, 2-[N-methyl-N-((6-methoxy-naphth-2-yl)-eth-2-yl)-amino-prop-3-yl]-6,7-dimethoxy-1,2,3,4-tetrahydro-isoquinolin-1-one, 2-[N-methyl-N-((2-methyl-naphth-1-yl)-methyl)-amino-prop-3-yl]-6,7-methylenedioxy-1,2,3,4-tetrahydro-isoquinolin-1-one, 2-[N-methyl-N-((naphth-2-oxy)-but -4-yl)-amino-prop-3-yl]-6,7-dimethyl-1,2,3,4-tetrahydro-isoquinolin-1-one, 2-[N-methyl-N-((naphth-1-yl)-prop-3-yl)-amino-prop-3-yl]-6,7-dimethoxy-1,2,3,4-tetrahydro-isoquinolin-1-one, 2-[N-methyl-N-((naphth-1-yl)-prop-3-yl)-amino-prop-3-yl]-6,7-methylenedioxy-1,2,3,4-tetrahydro-isoquinolin-1-one, 2-[N-methyl-N-((naphth-1-yl)-prop-3-yl)-amino-prop-3-yl]-6,7-dimethyl-1,2,3,4-tetrahydro-isoquinolin-1-one.

2-[N-methyl-N-((naphth-1-yl)-eth-2-yl)-amino-prop-3-yl]-6,7-dimethoxy-1,2,3,4-tetrahydro-isoquinolin-1-one, 2-[N-methyl-N-((naphth-1-yl)-eth-2-yl)-amino-prop-3-yl]-6,7-methylenedioxy-1,2,3,4-tetrahydro-isoquinolin-1-one, 2-[N-methyl-N-((naphth-1-yl)-eth-2-yl)-amino-prop-3-yl]-6,7-dimethyl-1,2,3,4-tetrahyro-isoquinolin-1-one, 2-[N-methyl-N-((naphth-2-yl)-eth-2-yl)-amino-prop-3-yl]-6,7-dimethoxy-1,2,3,4-tetrahydro-isoquinoline,
2-[N-methyl-N-((naphth-2-yl)-eth-2-yl)-amino-prop-3-yl]-6,7-methylenedioxy-1,2,3,4-tetrahydro-isoquinoline,
2-[N-methyl-N-((naphth-2-yl)-eth-2-yl)-amino-prop-3-yl]-6,7-dimethyl-1,2,3,4-tetrahydro-isoquinoline,
2-[N-methyl-N-((naphth-1-yl)-eth-2-yl)-amino-prop-3-yl]-6,7-dimethoxy-1,2,3,4-tetrahydro-isoquinoline,
2-[N-methyl-N-((naphth-1-yl)-eth-2-yl)-amino-prop-3-yl]-6,7-methylenedioxy-1,2,3,4-tetrahydro-isoquinoline,
2-[N-methyl-N-((naphth-1-yl)-eth-2-yl)-amino-prop-3-yl]-6,7-dimethyl-1,2,3,4-tetrahydro-isoquinoline,
2-[N-methyl-N-((2-methyl-naphth-1-yl)-methyl)-amino-prop-3-yl]-6,7-dimethyl-1,2,3,4-tetrahydro-isoquinoline,
[N-methyl-N-((2-methyl-naphth-1-yl)-methyl)-amino-prop-3-yl]-6,7-methylenedioxy-1,2,3,4-tetrahydro-isoquinoline,
2-[N-methyl-N-((5-methyl-6-methoxy-naphth-2-yl)-eth-2-yl)-amino-prop-3-yl]-6,7-dimethyl-1,2,3,4-tetrahydro-isoquinoline,
2-[N-methyl-N-((5-methyl-6-methoxy-naphth-2-yl)-eth-2-yl)-amino-prop-3-yl]-6,7-methyleneoxy-1,2,3,4-tetrahydro-isoquinoline,
2-[N-methyl-N-((6-methoxy-naphth-2-yl)-eth-2-yl)-amino-prop-3-yl]-6,7-dimethoxy-1,2,3,4-tetrahydro-isoquinoline,
2-[N-methyl-N-((6-methoxy-naphth-2-yl)-eth-2-yl)-amino-prop-3-yl]-6,7-methylenedioxy-1,2,3,4-tetrahydro-isoquinoline,
2-[N-methyl-N-((6-methoxy-naphth-2-yl)-eth-2-yl)-amino-prop-3-yl]-6,7-dimethyl-1,2,3,4-tetrahydro-isoquinoline,
2-[N-methyl-N-((naphth-2-yl)-prop-2-yl)-amino-prop-3-yl]-6,7-dimethoxy-1,2,3,4-tetrahydro-isoquinoline,
2-[N-methyl-N-((naphth-2-yl)-prop-3-yl)-amino-prop-3-yl]-6,7-methylenedioxy-1,2,3,4-tetrahydro-isoquinoline,
2-[N-methyl-N-((naphth-2-yl)-prop-3-yl)-amino-prop-3yl]-6,7-dimethyl-1,2,3,4-tetrahydro-isoquinoline,
2-[N-methyl-N-((naphth-2oxy)-but-4-yl)-amino-prop-3-yl]-6,7-methylenedioxy-1,2,3,4-tetrahydro-isoquinoline,
2-[N-methyl-N-((naphth-2-oxy)-but-4-yl)-amino-prop-3-yl]-6,7-dimethyl-1,2,3,4-tetrahydro-isoquinoline,
2-[N-methyl-N-((naphth-1-yl)-prop-3-yl)-amino-prop-3-yl]-6,7-dimethoxy-1,2,3,4-tetrahydro-isoquinoline,
2-[N-methyl-N-((naphth-1-yl)-prop-3-yl)-amino-prop-3-yl]-6,7-methylenedioxy-1,2,3,4-tetrahydro-isoquinoline,
2-[N-methyl-N-((naphth-1-yl)-prop-3-yl))-amino-prop-3-yl]-6,7-dimethyl-1,2,3,4-tetrahydro-isoquinoline,
2-[N-methyl-N-((naphth-2-yl)-prop-3-yl)-amino-prop-3-yl]-6,7-dimethoxy-1,2,3,4-tetrahydro-isoquinoline,
2-[N-methyl-N-((naphth-2-yl)-prop-2-yl)-prop-2-yl)-amino-prop-3-yl]-6,7-methylenedioxy-1,2,3,4-tetrahydro-isoquinoline,
2-[N-methyl-N-((naphth-2-yl)-prop-3-yl)-amino-prop-3-yl]-6,7-dimethyl-1,2,3,4-tetrahydro-isoquinoline,
2-[N-methyl-N-((2-methyl-naphth-1-yl)-eth-2-yl)-amino-prop-3-yl]-6,7-dimethoxy-1,2,3,4-tetrahydro-isoquinoline,
2-[N-methyl-N-((2-methyl-naphth-1-yl)-eth-2-yl)-amino-prop-3-yl]-6,7-methylenedioxy-1,2,3,4-tetrahydro-isoquinoline,
2-[N-methyl-N-((2-methyl-naphth-1-yl)-eth-2-yl)-amino-prop-3-yl]-6,7-dimethyl-1,2,3,4-tetrahydro-isoquinoline,
3-[N-methyl-N-((6-methoxy-5-methyl-naphth-2-yl)-eth-2-yl)amino-prop-3-yl]-7,8-dimethyl-1,3,4,5-tetrahydro-2H-3-benzazepin-2-one,
3-[N-methyl-N-((6-methoxy-naphth-2-yl)-eth-2-yl)-amino-prop-3-yl]-7,8-methylenedioxy-1,3,4,5tetrahydro-2H-3-benzazepin-2-one,
3-[N-methyl-N-((6-methoxy-naphth-2-yl)-prop-3-yl)-aminoprop-3-yl]-7,8-methylenedioxy-1,3,4,5-tetrahydro-2H-3-benzazepin-2-one,
2-[N-methyl-N-((2-methyl-naphth-1-yl)-eth-2yl)-amino-eth-2-yl]-7,8-dimethyl-1,3,4,5-tetrahydro-2H-3-benzazepin-2-one,
3-[N-methyl-N-((naphth-2-oxy)-but-4-yl)-amino-prop-3-yl]-7,8-methylenedioxy-1,3,4,5-tetrahydro-2H-3-benzazepin-2-one,
3-[N-methyl-N-((2-methyl-naphth-1-yl)-methyl)-amino-prop-3-yl]-7,8-dimethyl-1,3,4,5-tetrahydro-2H-3-benzazepin-2-one,
3-[N-methyl-N-((6-methoxy-naphth-2-yl)-prop-3-yl)-amino-prop-3-yl]-7,8-methylenedioxy-1,3,4,5-tetrahydro-2H-3-benzazepine,
3-[N-methyl-N-((naphth-2-oxy)-but-4-yl)-amino-prop-3-yl]-7,8-dimethyl-1,3,4,5-tetrahydro-2H-3-benzazepin-2-one,
2-[N-methyl-N-((6-methoxy-5-methyl-naphth-2-yl)-eth-2-yl)-amino-eth-2-yl]-7,8-methylenedioxy-1,3,4,5-tetrahydro-2H-3-benzazepin-2-one,
2-[N-methyl-N-((6-methoxy-5-methyl-naphth-2-yl)-eth-2-yl)-amino-eth-2-yl]-7,8-methylenedioxy-1,3,4,5-tetrahydro-2H-3-benzazepine,
3-[N-methyl-N-((6-methoxy-naphth-2-yl)-eth-2yl)-amino-prop-3-yl]-7,8-dimethyl-1,3,4,5-tetrahydro-2H-3-benzazepin-2-one,
3-[N-methyl-N-((6-methoxy-naphth-2-yl)-eth-2-yl)-aimino-prop-3-yl]-7,8-dimethyl-1,3,4,5-tetrahydro-2H-3-benzazepine,
2-[N-methyl-N-((naphth-1-yl)-eth-2-yl)-amino-eth-2-yl]-7,8-methylenedioxy-1,3,4,5-tetrahydro-2H-3-benzazepin-2-one,
2-[N-methyl-N-((naphth-1-yl)-eth-2-yl)-amino-eth-2-yl]-7,8-methylenedioxy-1,3,4,5-tetrahydro-2H-3-benzazepine,
3-[N-methyl-N-((2-methyl-naphth-1-yl)-eth-2-yl)-amino-prop-3-yl]-7,8-methylenedioxy-1,3,4,5-tetrahydro-2H-3-benzazepin-2-one,
3-[N-methyl-N-((2-methyl-naphth-1-yl)-eth-2-yl)-amino-prop-3-yl]-7,8-methylenedioxy-1,3,4,5-tetrahydro-2H-3benzazepine,
2-[N-methyl-N-((6-methoxy-naphth-2-yl)-eth-2-yl)-amino-eth-2-yl]-5-methyl-phthalimidine,
2-[N-methyl-N-((2-methyl-naphth-1-yl)-eth-2-yl)-amino-eth-2-yl]-5-methyl-1,3-dihydro-isoindole,
2-[N-methyl-N-((5-methyl-6-methoxy-naphth-2-yl)-eth-2-yl)-amino-eth-2-yl]-5,6-dimethyl-phthalimidine,
2-[N-methyl-N-((naphth-1-yl)-eth-2-yl)-amino-eth-2-yl]-5,6-dimethyl-1,3-dihydro-isoindole,
2-[N-methyl-N-((6-methoxy-naphth-2-yl)-eth-2-yl)-amino-eth-2-yl]-5,6-methylenedioxy-phthalimidine,
2-[N-methyl-N-((5-methyl-6-methoxy-naphth-2-yl)-eth-2-yl)-amino-eth-2-yl]-5,6-methylenedioxy-phthalimidine,
2-[N-methyl-N-((2-methyl-naphth-1-yl)-eth-2-yl)-amino-eth-2-yl]-5,6-methylenedioxy-1,3-dihydro-isoindole, 2-[N-methyl-N-((5-methyl-6-methoxy-naphth-2-yl)-eth-2-yl)-amino-eth-2-yl]-5,6-methylenedioxy-phthalimidine, 2-[N-methyl-N-((5-methyl-6-methoxy-naphth-2-yl)-eth-2-yl)-amino-prop-3-yl]-5,6-dimethyl-phthalimidine, 2-[N-methyl-N-((naphth-1-yl)-eth-2-yl)-amino-prop-3-yl]-5,6-methylenedioxy-phthalimidine, 2-[N-methyl-N-((6-methoxy-naphth-2-yl)-eth-2-yl)-amino-prop-3-yl]-5,6-methylenedioxy-1,3-dihydro-isoindole, 2-[N-methyl-N-((2-methyl-naphth-1-yl)-prop-3-yl)-amino-eth-2-yl]-5,6-dimethyl-phthalimidine, 2-[N-methyl-N-((6-methoxy-naphth-2-yl)-but-4-yl)-amino-prop-3-yl]-5,6-dimethyl-phthalimidine, 2-[N-methyl-N-((2-methyl-naphth-1-yl)-but-4-yl)-amino-prop-3-yl]-5,6-dimethyl-phthalimidine, 2-[N-methyl-N-((6-methoxy-naphth-2-yl)-but-4-yl)-amino-prop-3-yl]-5,6-methylenedioxy-phthalimidine, 2-[N-methyl-N-((5-methyl-6-methoxy-naphth-2-yl)-oxybut-4-yl)-amino-prop-3-yl]-5,6-methylenedioxy-phthalimidine, 2-[N-methyl-N-((6-methoxy-naphth-2-yl)-oxyprop-3-yl)-amino-eth-2-yl]-5,6-dimethoxy-phthalimidine, 2-[N-methyl-N-((6-methoxy-naphth-2-yl)-oxyprop-3-yl)-amino-prop-3-yl]-5,6-dimethoxy-phthalimidine, 2-[N-methyl-N-((naphth-1-yl)-oxyprop-3-yl)-amino-prop-1-yl]-5,6-methylenedioxy-phthalimidine, 2-[N-methyl-N-((naphth-1-yl)-pent-5-yl)-amino-eth-2-yl]-5,6-dimethyl-phthalimidine, 2-[N-methyl-N-((2-methyl-naphth-1-yl)-pent-5-yl)-amino-eth-2-yl]-5,6-methylenedioxy-phthalimidine, 2-[N-methyl-N-((2-methyl-naphth-1-yl)-pent-5-yl)-amino-prop-3-yl]-5,6-dimethyl-phthalimidine, 2-[N-methyl-N-((5-methyl-6-methoxy-naphth-2-yl)-pent-5-yl)-amino-prop-3-yl]-5,6-methylenedioxy-phthalimidine.

However, preferred compounds of general formula I above are those wherein

A, L and n are as hereinbefore defined,

E represents an ethylene or n-propylene group,

G represents a straight chained alkylene group with 1 to 4 carbon atoms optionally substituted by a methyl group, $R_1$ represents a methyl or methoxy group, $R_2$ represents a methyl or methoxy group or $R_1$ and $R_2$ together represent a methylenedioxy group, $R_3$ represents a methyl group, $R_4$ represents a hydrogen atom or methyl group, $R_5$ represents a hydrogen atom or a methyl or methoxy group, $R_6$ represents a hydrogen atom or a methoxy group, and the enantiomers and acid addition salts thereof.

However, particularly preferred compounds of general formula I are those wherein n represents the number 1 or 2, A represents a —$CH_2$—, —CO— or —$CH_2CO$— group, E represents an n-propylene group, G represents an ethylene group, L represents a bond, $R_1$ and $R_2$ each represent a methoxy group or together represent a methylenedioxy group, $R_3$ represents a methyl group, $R_4$ represents a hydrogen atom, $R_5$ represents a hydrogen atom or a methyl or methoxy group and $R_6$ represents a hydrogen atom or a methoxy group, and the acid addition salts thereof.

According to the invention the new compounds are obtained by the following processes:

(a) Reacting a compound of general formula

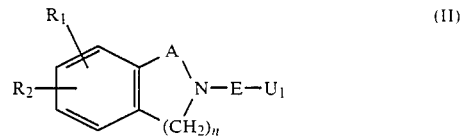

with a compound of general formula

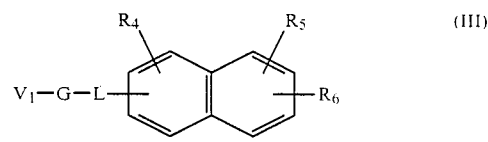

wherein $R_1$, $R_2$, $R_4$ to $R_6$, A, G, L and n are defined as hereinbefore, one of the groups $U_1$ or $V_1$ represents an $R_3$—NH— group, wherein $R_3$ is defined as hereinbefore, and the other group $U_1$ or $V_1$ represents a nucleophilically exchangeable group such as a halogen atom or a sulphonyloxy group, e.g. a chlorine, bromine or iodine atom, a methanesulphonyloxy, benzenesulphonyloxy, p-toluenesulphonyloxy or ethoxysulphonyloxy group.

The reaction is conveniently carried out in a solvent or mixture of solvents such as acetone, diethyl ether, methyl formamide, dimethyl formamide, dimethylsulphoxide, benzene, chlorobenzene, tetrahydrofuran, benzene/tetrahydrofuran, dioxane or in an excess of the compounds of general formulae II and/or III used and optionally in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide, an alkali metal hydride such as sodium hydride, a tertiary organic base such as triethylamine or pyridine, whilst the latter may simultaneously also serve as solvent, or a reaction accelerator such as potassium iodide, depending on the reactivity of the nucleophilically exchangeable group, conveniently at temperatures of between 0° and 150° C., preferably at temperatures of between 50° and 120° C., e.g. at the boiling temperature of the solvent used. The reaction may, however, also be carried out without a solvent. It is particularly advantageous to carry out the reaction in the presence of a tertiary organic base or an excess of the amine of general formula II or III used.

(b) Reacting a compound of general formula

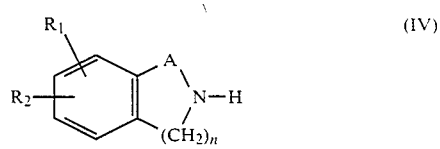

wherein $R_1$, $R_2$, A and n are as hereinbefore defined, with a compound of general formula

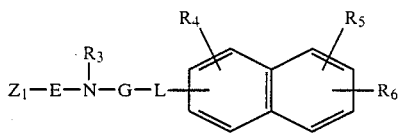

wherein
$R_3$ to $R_6$, E, G and L are as hereinbefore defined, and
$Z_1$ represents a nucleophilically exchangeable group such as a halogen atom or a sulphonyloxy group, e.g. a chlorine, bromine or iodine atom or a methanesulphonyloxy, p-toluenesulphonyloxy or ethoxysulphonyloxy group.

The reaction is conveniently carried out in a solvent or mixture of solvents such as methyl formamide, dimethyl formamide, dimethyl sulphoxide, benzene, chlorobenzene, tetrahydrofuran, benzene/tetrahydrofuran or dioxane in the presence of an acid binding agent, e.g. an alkoxide such as potassium tert.butoxide, an alkali metal hydroxide such as sodium or potassium hydroxide, an alkali metal carbonate such as potassium carbonate, an alkali metal amide such as sodium amide or an alkali metal hydride such as sodium hydride, conveniently at temperatures of between 0° and 150° C., preferably at temperatures of between 0° and 50° C.

(c) Reductively aminating a compound of general formula

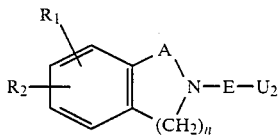

in the presence of a compound of general formula

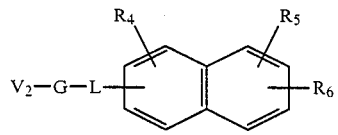

wherein $R_1$, $R_2$, $R_4$ to $R_6$, A, E, G, L and n are as hereinbefore defined,
one of the groups $U_2$ or $V_2$ represents an $R_3$—NH group, wherein $R_3$ is defined as hereinbefore, and
the other group $U_2$ or $V_2$, together with a hydrogen atom of the adjacent carbon atom of group G or E, wherein E and G are each defined as hereinbefore, represents an oxygen atom.

The reduction is carried out in a suitable solvent such as methanol, ethanol, diethyl ether, tetrahydrofuran, dioxane, ethyl acetate or ethanol/ethyl acetate with a metal hydride such as lithium aluminium hydride, diborane, sodium cyanoborohydride or borane/dimethyl sulphide, but preferably with sodium borohydride or with hydrogen in the presence of a hydrogenation catalyst such as platinum, palladium/charcoal or Raney nickel under a hydrogen pressure of from 1 to 5 bar or with hydrazine in the presence of a hydrogenation catalyst such as platinum, palladium/charcoal or Raney nickel, at temperatures of between 0° and 50° C., preferably at ambient temperature. During the reduction with a complex metal hydride such as lithium aluminium hydride, diborane or diborane/dimethyl sulphide, a carbonyl function present in the group A may be reduced simultaneously to form a methylene group or during catalytic hydrogenation a double bond present in group A may also be reduced.

(d) Reduction of an acid amide of general formula

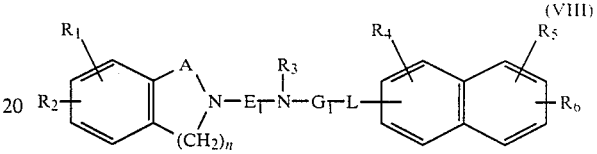

wherein
$R_1$ to $R_6$, A, L and n are defined as hereinbefore,
one of the groups $E_1$ or $G_1$ has the meanings given for E or G hereinbefore, and
the other group $E_1$ or $G_1$ also has the meanings given for E or G hereinbefore, but a methylene group adjacent to a nitrogen atom must be replaced by a carbonyl group.

The reduction is preferably carried out in a suitable solvent such as methanol, ethanol, diethyl ether or tetrahydrofuran in the presence of a metal hydride such as sodium borohydride, lithium aluminium hydride, diborane, borane/dimethyl sulphide or sodium cyanoborohydride, but preferably with sodium borohydride in methanol or ethanol, at between 0° and 40° C., but preferably at ambient temperature.

During the reduction with a complex metal hydride such as lithium aluminium hydride, diborane or borane/dimethyl sulphide, any carbonyl function present in the group A may be reduced simultaneously to form a methylene group.

(e) In order to prepare compounds of general formula I, wherein A represents a —CH$_2$CS— group:
reacting a compound of general formula

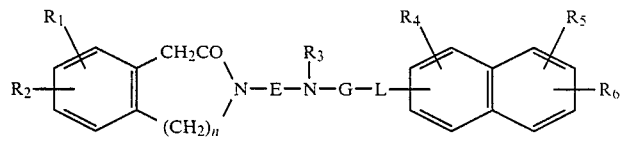

wherein
$R_1$ to $R_6$, E, G, L and n are defined as hereinbefore, with a sulphurising agent.

The reaction is carried out with a sulphurising agent such as phosphorous pentasulphide or 2,4-bis(4-methoxyphenyl)-1,3-dithia-2,4-diphosphetan-2,4-disulphide appropriately in a solvent such as toluene or xylene at temperatures of between 50° and 150° C., e.g. at the boiling temperature of the reaction mixture.

(f) In order to prepare compounds of general formula I, wherein the —G—L— group represents an ethylene group optionally substituted by an alkyl group:

reacting a compound of general formula

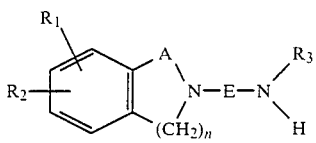

wherein $R_1$ to $R_3$, A, E and n are defined as hereinbefore, with a vinyl compound of general formula

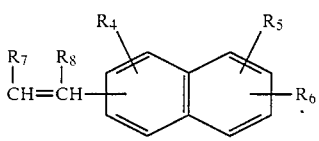

wherein $R_4$ to $R_6$ are defined as hereinbefore, one of the groups $R_7$ or $R_8$ represents a hydrogen atom and the other group $R_7$ or $R_8$ represents an alkyl group with 1 to 3 carbon atoms.

The reaction is preferably carried out in a solvent such as methanol, ethanol, dioxane or tetrahydrofuran at temperatures of between 0° and 50° C., preferably by standing at ambient temperature.

(g) In order to prepare compounds of general formula I, wherein

A represents a —CH$_2$—, —CH$_2$CH$_2$— or —CH=CH— group, and n represents the number 1: reduction of a compound of general formula

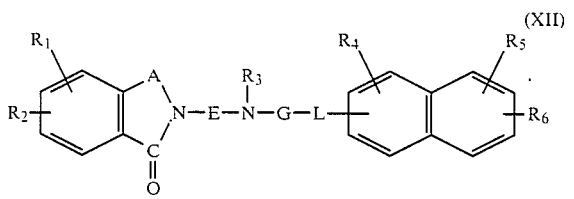

wherein $R_1$ to $R_6$, A, E, G and L are defined as hereinbefore.

The reduction is preferably carried out with a metal hydride such as lithium aluminium hydride or diborane or with a complex of borane and a thioether, e.g. with a borane-dimethyl sulphide complex, in a suitable solvent such as diethyl ether or tetrahydrofuran at temperatures of between 0° and 50° C., but preferably at temperatures of between 10° and 25° C. Any carbonyl function present in the group A is simultaneously reduced to form the methylene group.

In the reaction described above, any reactive groups present such as amino or imino groups can be protected during the reaction by conventional protecting groups which are split off again after the reaction.

Examples of suitable protecting groups for a hydroxy group include the trimethylsilyl, acetyl, benzoyl, benzyl and tetrahydropyranyl groups and examples of protecting groups for an imino or amino group include the acetyl, benzoyl, ethoxycarbonyl and benzyl groups.

The optional subsequent splitting off of any protecting group used is preferably carried out hydrolytically in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures of between 0° and 100° C., preferably at the boiling temperature of the reaction mixture. However, a benzyl group is preferably split off hydrogenolytically, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of between 0° and 50° C., but preferably at ambient temperature, under a hydrogen pressure of from 1 to 7 bar, preferably from 3 to 5 bar.

The compounds of general formula I obtained may, if they have a chiral center, be resolved into their diastereomers by conventional methods, for example by column chromatography, and into their enantiomers, for example by column chromatography on a chiral phase or by crystallisation with optically active acids, e.g. with D- or L-monomethyltartaric acid, D- or L-diacetyltartaric acid, D- or L-tartaric acid, D- or L-lactic acid or D- or L-camphoric acid.

The compounds of general formula I obtained may also be converted into their acid addition salts, particularly their physiologically acceptable acid addition salts with inorganic or organic acids, for pharmaceutical use. Examples of suitable acids include hydrochloric, hydrobromic, sulphuric, phosphoric, acetic, lactic, citric, tartaric, succinic, maleic and fumaric acid.

Some of the compounds of general formulae II to XII used as starting materials are known from the literature, whilst others may be obtained by methods known per se.

Thus, for example, a benzazepine of general formula IV unsubstituted in the 3-position is obtained by cyclisation of a corresponding compound, e.g. by cyclising a compound of general formula

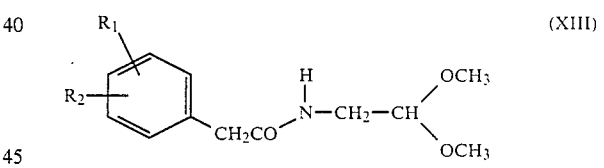

or general formula

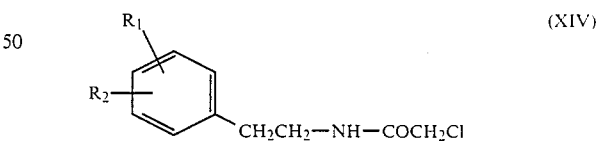

optionally with subsequent catalytic hydrogenation and/or reduction of the carbonyl group, e.g. with sodium borohydride/glacial acetic acid (see EP-A1-0007070, EP-A1-0065229 and EP-A1-0109639) and/or oxidation, e.g. with selenium dioxide or by reacting a suitably substituted phenylethylamine with chloroacetic acid chloride and subsequent cyclisation (see Tetrahedron Letters 21, 1393 (1980)).

An isoquinolin-1-one of general formula IV is obtained by reacting a correspondingly substituted phenylethylamine with a chloroformate and subsequent cyclisation (see Helv. Chim. Acta 47, 2092 (1964)) or by converting a correspondingly substituted β-phenylpropionic acid into the isocyanate with subsequent cyclisation (see Chem. Pharm. Bull. Jap. 24, 2976 (1979)).

A phthalimidine of general formula II or a 1H-phthalimidine of general formula IV is obtained by reduction of a corresponding phthalimide, e.g. with zinc powder/glacial acetic acid.

A starting compound of general formula II, VI or X is obtained by alkylation of a compound of general formula IV with a corresponding haloalkane, if necessary followed by reaction with a corresponding amine.

A starting compound of general formula III is obtained by reacting a suitable hydroxy compound with a corresponding sulphonic acid halide or a corresponding halogenating agent and if necessary subsequently reacting with a corresponding amine, and an amino compound of general formula VII thus obtained may be converted into a compound of general formula V by reacting with a corresponding dihaloalkane.

A carbonyl compound of general formula VI is obtained by reacting a compound of general formula IV with a corresponding haloalkanal and a carbonyl compound of general formula VII is obtained by oxidation of a suitable hydroxy compound.

A compound of general formula VIII is obtained by reacting a corresponding amine with a corresponding carboxylic acid, a compound of general formula IX or XII is obtained by alkylating a corresponding NH compound with a corresponding alkyl halide, and a vinyl compound of general formula X is obtained by dehydrating a corresponding hydroxy compound.

As already mentioned at the beginning, the new compounds of general formula I and the physiologically acceptable acid addition salts thereof with inorganic or organic acids have valuable pharmacological properties, particularly an especially long lasting heart rate lowering activity and the effect of reducing the $O_2$-requirement of the heart, whilst having few central side effects.

The following compounds, for example:

A = 3-[N-methyl-N-((6-methoxy-naphth-2-yl)-eth-2-yl)-amino-prop-3-yl]-7,8-dimethoxy-1,3,4,5-tetrahydro-2H-3-benzazepin-2-one, B = 3-[N-methyl-N-((6-methoxy-5-methyl-naphth-2-yl)-eth-2-yl)-amino-prop-3-yl]-7,8-dimethoxy-1,3,4,5-tetrahydro-2H]-benzazepin-2-one, C = 3-[N-methyl-N-((naphth-2-yl)-eth-2-yl)-amino-prop-3-yl]-7,8-dimethoxy-1,3,4,5-tetrahydro-2H-benzazepin-2-one, D = 2-[N-methyl-N-((naphth-2-yl)-eth-2-yl)-amino-prop-3-yl]-6,7-methylenedioxy-1,2,3,4-tetrahydro-isoquinolin-1-one hydrochloride, and E = 2-[N-methyl-N-((5-methyl-6-methoxy-naphth-2-yl)-eth-2-yl)-amino-prop-3-yl]-6,7-dimethoxy-1,2,3,4-tetrahydroisoquinolin-1-one hydrochloride, were tested for their biological properties as follows:
Effect on heart rate in rats:

The effect of the test substances on heart rate was investigated on 2 rats with an average weight of 250–300 g for each dosage. The rats were anaesthetised with pentobarbital (50 mg/kg i.p. and 20 mg/kg s.c.). The test substances were injected in aqueous solution into the jugular vein (0.1 ml/100 g).

The blood pressure was measured using a cannula tied into a carotid artery and the heart rate was recorded from an ECG (IInd or IIIrd derivation) obtained with needle electrodes. The heart rate of the animals in the control period was between 350 and 400 beats per minute (b/min).

The following Table contains the results obtained:

| Substance | Dosage [mg/kg] | Lowering of heart rate measured 20 minutes after administration of substance [b/min] |
| --- | --- | --- |
| A | 5.0 | −184 |
| B | 5.0 | −177 |
| C | 5.0 | −170 |
| D | 5.0 | −163 |
| E | 5.0 | −91 |

The compounds prepared according to the invention have no toxic effects of any kind when administered in therapeutic doses. Thus, for example, when substances A to E are administered intravenously to mice, even in a high dose of 20 mg/kg, no toxic side effects could be detected other than a slight sedation.

In view of their pharmacological properties the compounds prepared according to the invention are suitable for the treatment of sinus tachycardia of various origins and for the prevention and treatment of ischaemic heart disease.

The dosage required to achieve such an effect is conveniently 0.01 to 0.2 mg/kg of body weight, preferably 0.03 to 0.15 mg/kg of body weight, once to twice a day. For this purpose, the compounds of general formula I and the physiologically acceptable acid addition salts thereof with inorganic or organic acids, prepared according to the invention, optionally together with other active substances, may be incorporated together with one or more inert conventional carriers and/or diluents, e.g. corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propylene glycol, carboxymethyl cellulose or fatty substances such as hard fat or suitable mixtures thereof, into conventional galenic preparations such as plain or coated tablets, capsules, powders, suspensions, drops, ampoules, syrups or suppositories.

The following Examples are intended to illustrate the invention:

EXAMPLE 1

2-[N-Methyl-N-((2-methyl-naphth-1-yl)-eth-2-yl)-amino-prop-3-yl]-6,7-dimethoxy-1,2,3,4-tetrahydro-isoquinolin-1-one hydrochloride A mixture of 1.13 g (4 mmol) of 2-(3-chloropropyl)-6,7-dimethoxy-1,2,3,4-tetrahydro-isoquinolin-1-one, 1.04 g (4.4 mmol) of N-methyl-2-(2-methyl-naphth-1-yl)-ethylamine hydrochloride and 1.5 ml of N-ethyl-diisopropylamine is refluxed for 2 hours. The excess N-ethyl-diisopropylamine is evaporated off in vacuo and the residue remaining is dissolved in a mixture of methylene chloride and 2 molar sodium hydroxide solution. The organic phase is separated, washed with water, dried over magnesium sulphate, evaporated down in vacuo and purified over a 150 g silica gel column (0.062–0.2 mm) with methylene chloride and then with increasing amounts of ethanol (up to 5%). The hydrochloride is precipitated from a solution in acetone with ethereal hydrochloric acid and then recrystallised from acetone.

Yield: 0.67 g (34.7% of theory),
Melting point: 130°–132° C.
Calculated: C 69.62, H 7.20, N 5.80, Cl 7.34, Found: C 69.53, H 7.46, N 5.84, Cl 7.64.

EXAMPLE 2

2-[N-Methyl-N-((naphth-2-yl)-prop-2-yl)-amino-prop-3-yl]-6,7-dimethoxy-1,2,3,4-tetrahydro-isoquinolin-1-one hydrochloride 0.83 g (4 mmol) of 6,7-dimethoxy-1,2,3,4-tetrahydro-isoquinolin-1-one is dissolved in 15 ml of dimethyl formamide and 0.49 g (4.4 mmol) of potassium tert.butoxide are added with stirring. The potassium salt is precipitated after an exothermic reaction (up to about 40° C.) after about 30 minutes. It is cooled to 0° C. and 1.4 g (4.4 mmol) of 3-[N-methyl-(naphth-2-yl)-prop-2-yl-amino]-propyl bromide is added. After 4 hours at this temperature it is poured onto ice water and extracted with ethyl acetate. The organic phase is washed with water, dried over magnesium sulphate, concentrated by evaporation in vacuo and purified over a silica gel column (0.063–0.2 mm) with methylene chloride and then with increasing amounts of ethanol (up to 5%). The hydrochloride is precipitated from a solution in acetone with ethereal hydrochloric acid and is then recrystallised from acetone.

Yield: 0.65 g (33.7% of theory),
Melting point: 133°–135° C.
Calculated: C 69.62, H 7.30, N 5.80, Cl 7.34, Found C 69.35, H 7.41, N 5.89, Cl 7.52.

EXAMPLE 3

2-[N-Methyl-N-((5-methyl-6-methoxy-naphth-2-yl)-eth-2-yl)-amino-prop-3-yl]-6,7-dimethoxy-1,2,3,4-tetrahydro-isoquinolin-1-one hydrochloride 0.83 g (4 mmol) of 6,7-dimethoxy-1,2,3,4-tetrahydro-isoquinolin-1-one is dissolved in 15 ml of dimethyl formamide and 0.49 g (4.4 mmol) of potassium tert.butoxide are added with stirring. The potassium salt is precipitated after about 30 minutes after an exothermic reaction (up to about 40° C). It is cooled to 0° C. and 1.9 g (4.4 mol) of benzenesulphonic acid 3-[N-methyl-(5-methyl-6-methoxy-naphth-2-yl)-eth-2-yl-propyl-amino]-propyl ester is added. After 4 hours at this temperature it is poured onto ice water and extracted with ethyl acetate. The organic phase is washed with water, dried over magnesium sulphate, evaporated down in vacuo and purified over a silica gel column (0.063–0.2 mm) with methylene chloride and then with increasing amounts of ethanol (up to 5%). The hydrochloride is precipitated from a solution in acetone with etheral hydrochloric acid and is then recrystallised from acetone.

Yield: 0.45 g (21.9% of theory),
Melting point: 187°–189° C.
Calculated: C 67.89, H 7.27, N 5.46, Cl 6.91, Found C 67.70, H 7.28, N 5.44, Cl 6.88.

EXAMPLE 4

3-[N-Methyl-N-((6-methoxy-naphth-2-yl)-eth-2-yl)-amino-prop-3-yl]-7,8-dimethoxy-1,3,4,5-tetrahydro-2H-3-benzazepin-2-one A mixture of 0.66 g (2.5 mmol) of 2-(2-bromoethyl)-6-methoxy-naphthalene and 1.46 g (5 mmol) of 3-(N-methyl-amino-prop-3-yl)-7,8-dimethoxy-1,3,4,5-tetrahydro-2H-3-benzazepin-2-one is heated to 100° C. for 90 minutes. After cooling, the crude product is purified over 70 g of aluminium oxide (neutral, activity II-III) with methylene chloride and then with increasing amounts of ethanol (up to 0.25%).

Yield: 0.45 g (37.8% of theory),
M.p.: 93°–96° C.,
Calculated: C 73.08, H 7.61, N 5.88, Found: C 73.20, H 7.58, N 5.71.

EXAMPLE 5

2-[N-Methyl-N-((naphth-2-oxy)-but-4-yl)-amino-prop-3-yl]-7,8-dimethoxy-1,2,3,4-tetrahydro-isoquinolin-1-one hydrochloride 1.05 g (4 mmol) of 2-(2-formyl-ethyl)-6,7-dimethoxy-1,2,3,4-tetrahydro-isoquinolin-1-one and 0.92 g (4 mmol) of N-methyl-4-(naphth-2-oxy)-butylamine are hydrogenated in 50 ml of ethanol in the presence of 0.2 g of 10% palladium on activated charcoal at 70° C. under 5 bar until the calculated quantity of hydrogen has been taken up. The catalyst is filtered off and the filtrate is evaporated to dryness in vacuo. The hydrochloride is precipitated from a solution in acetone with ethereal hydrochloric acid and is then recrystallised from acetone/ether.

Yield: 0.6 g (60% of theory),
Melting point: 135°–136° C.
Calculated: C 67.89, H 7.27, N 5.46, Cl 6.91, Found: C 67.81, H 7.22, N 5.42, Cl 6.79.

The reduction may also be carried out with sodium borohydride in ethanol at ambient temperature or boiling temperature.

EXAMPLE 6

2-[N-Methyl-N-((2-methyl-naphth-1-yl)-methyl)-amino-prop-3-yl]-6,7-dimethoxy-1,2,3,4-tetrahydro-isoquinolin-1-one hydrochloride (a)

2-[N-Methyl-N-(2-methyl-naphth-1-yl)-amido-prop-3-yl]-6,7-dimethoxy-1,2,3,4-tetrahydro-isoquinolin-1-one 0.71 g (4.4 mmol) of N,N'-carbonyldiimidazole are added to a solution of 0.82 g (4.4 mmol) of 2-methyl-1-naphthoic acid in 20 ml of dimethyl formamide. The imidazolide of the acid is formed over a period of about 30 minutes with the evolution of carbon dioxide. 1.06 g (4 mmol) of 2-[N-methyl-amino-prop-3-yl]-6,7-dimethoxy-1,2,3,4-tetrahydro-isoquinolin-1-one are added and the resulting mixture is stirred for 2 hours at ambient temperature. The solvent is evaporated off in vacuo, the residue remaining is dissolved in a mixture of 2 molar sodium hydroxide solution and methylene chloride. The organic phase is washed with water, dried over magnesium sulphate and concentrated by evaporation in vacuo.

Crude yield: 1.3 g (67.3% of theory)

(b)

2-[N-Methyl-N-((2-methyl-naphth-1-yl)-methyl)-amino-prop-3-yl]-6,7-dimethoxy-1,2,3,4-tetrahydro-isoquinolin-1-one hydrochloride To a solution of 1.3 g (3 mmol) of 2-[N-methyl-N-(2-methyl-naphth-1-yl)-amino-prop-3-yl]-6,7-dimethoxy-1,2,3,4-tetrahydro-isoquinolin-1-one in 50 ml of tetrahydrofuran, 4.5 ml of a 1 molar borane-tetrahydrofuran complex in tetrahydrofuran are added and 0.55 ml (4.5 mmol) of boron trifluoride-diethyl etherate complex are added dropwise with stirring at ambient temperature. After 3 hours' reaction time, 5 ml of 6 molar hydrochloric acid are added dropwise, the mixture is refluxed for 0.5 hours and then the solvent is evaporated off in vacuo. The aqueous portion remaining is made alkaline with 2 molar sodium hydroxide solution and extracted with methylene chloride. The organic phase is washed with water, dried over sodium sulphate, evaporated down in vacuo and purified over a silica gel column (0.063–0.2 mm) with methylene chloride and then with increasing amounts of ethanol (up to 5%). The hydrochloride is precipitated from a solution in acetone with ethereal hydrochloric acid and is then recrystallised from acetone.

Yield: 0.21 g (10.2% of theory),
Melting point: 187°–189° C.
Calculated: C 69.15, H 7.09, N 5.97, Cl 7.56, Found: C 69.00, H 7.20, N 6.12, Cl 7.49.

EXAMPLE 7

3-[N-Methyl-N-((naphth-1-yl)-eth-2-yl)-amino-prop-3-yl]-7,8-dimethoxy-1,3,4,5-tetrahydro-2H-3-benzazepin-2-thione A mixture of 1.34 g (3 mmol) of 3-[N-methyl-N-((naphth-1-yl)-eth-2-yl)-amino-prop-3-yl]-7,8-dimethoxy-1,3,4,5-tetrahydro-2H-3-benzazepin-2-one and 0.61 g (1.5 mmol) of 2,4-bis-(4-methoxy-phenyl)-1,3-dithia-2,4-diphosphan-2,4-disulphide is refluxed for 90 minutes in 10 ml of toluene. The mixture is evaporated down in vacuo and the residue is purified over 120 g of aluminium oxide (neutral, activity II-III) with methylene chloride and then with increasing amounts of ethanol (up to 0.3%).

Yield: 0.97 g (69.8% of theory),
Calculated: C 72.68, H 7.41, N 6.05, S 6.93, Found: C 72.52, H 7.35, N 6.33, S 7.10.
$R_f$ value: 0.8 (aluminium oxide, neutral, methylene chloride/ethanol = 19:1)

EXAMPLE 8

3-[N-Methyl-N-((naphth-1-yl)-eth-2-yl)-amino-prop-3-yl]-7,8-dimethoxy-1,3,4,5-tetrahydro-2H-3-benzazepine dihydrochloride A mixture of 2.23 g (5 mmol) of 3-[N-methyl-N-((naphth-1-yl)-eth-2-yl)-amino-prop-3-yl]-7,8-dimethoxy-1,3,4,5-tetrahydro-2H-3-benzazepin-2-one and 0.57 g (15 mmol) of lithium aluminium hydride in 45 ml of absolute tetrahydrofuran is refluxed for 7 hours. After cooling it is decomposed with 0.57 ml of water, 0.57 ml of 10% sodium hydroxide solution and 1.71 ml of water, suction filtered and the filtrate is evaporated down in vacuo. The residue remaining is purified over 180 g of aluminium oxide (neutral, activity II-III) with methylene chloride and subsequently with increasing amounts of ethanol (up to 3%). The hydrochloride is precipitated from a solution in acetone with ethereal hydrochloric acid.

Yield: 0.96 g (37.9% of theory),
Melting point: 289°–290° C. (decomp.).
Calculated: C 66.53, H 7.58, N 5.54, Cl 14.03, Found: C 66.30, H 7.62, N 5.47, Cl 14.25.

EXAMPLE 9

2-[N-Methyl-N-((6-methoxy-naphth-2-yl)-eth-2-yl)-amino-prop-3-yl]-6,7-methylenedioxy-1,2,3,4-tetrahydro-isoquinolin-1-one hydrochloride 1.4 g (5 mmol) of 2-[N-methyl-amino-prop-3-yl]-6,7-methylenedioxy-1,2,3,4-tetrahydro-isoquinolin-1-one are dissolved in 20 ml of methanol and 1 g (5.5 mmol) of 6-methoxy-2-vinyl-naphthaline are added. After standing overnight at ambient temperature the solvent is evaporated off in vacuo and the residue is purified over a silica gel column (0.063–0.2 mm) with methylene chloride and subsequently with increasing amounts of ethanol (up to 5%). The hydrochloride is precipitated from a solution in acetone with ethereal hydrochloric acid and is then recrystallised from acetone/ether.

Yield: 0.28 g (11.6% of theory),
Melting point: 205°–207° C.
Calculated: C 67.14, H 6.47, N 5.80, Cl 7.34, Found: C 66.90, H 6.58, N 5.72, Cl 7.38.

EXAMPLE 10

2-[N-Methyl-N-((naphth-1-oxy)-eth-2-yl)-amino-prop-3-yl]-5,6-dimethoxy-phthalimidine 850 mg (1.9 mmol) of 2-[N-methyl-N-((naphth-1-oxy)-eth-2-yl)-amino-prop-3-yl]-5,6-dimethoxy-phthalimide are dissolved in 10 ml of glacial acetic acid. After the addition of 900 mg (13.8 mmol) of zinc powder the mixture is refluxed for 3 hours with stirring. The solvent is distilled off in vacuo and the residue is distributed in sodium hydroxide solution (w = 15%) and ethyl acetate. The organic phase is dried with sodium sulphate, evaporated down and purified over a silica gel flash column using methylene chloride/methanol as eluant, to produce 460 mg (56% of theory) of a yellow oil. This is dissolved in absolute methanol and the hydrochloride is precipitated with ethereal hydrochloric acid.

Yield: 380 mg (42% of theory),
$R_f$ value of the base: 0.35 (silica gel, methylene chloride/methanol = 9/1).

EXAMPLE 11

3-[N-Methyl-N-((naphth-2-yl)-eth-2-yl)-amino-prop-3-yl]-6,7-dimethoxy-1,2,3,4-tetrahydro-isoquinolin-1-one hydrochloride Prepared from 3-(3-chloropropyl)-6,7-dimethoxy-1,2,3,4-tetrahydro-isoquinolin-1-one and N-methyl-2-(naphth-2-yl)-ethylamine analogously to Example 1.

Yield: 50.8% of theory,
Melting point: 163°–165° C.
Calculated: C 69.14, H 7.09, N 5.97, Cl 7.56, Found: C 68.91, H 6.95, N 6.18, Cl 7.35.

EXAMPLE 12

2-[N-Methyl-N-((2-methyl-naphth-1-yl)-eth-2-yl)-prop-3-yl]-6,7-methylenedioxy-1,2,3,4-tetrahydro-isoquinolin-1-one hydrochloride Prepared from 2-(3-chloropropyl)-6,7-methylenedioxy-1,2,3,4-tetrahydro-isoquinolin-1-one hydrochloride and N-methyl-2-(2-methyl-naphth-1-yl)-ethylamine analogously to Example 1.

Yield: 36.6% of theory,
Melting point: 168°–170° C.
Calculated: C 69.44, H 6.69, N 5.99, Cl 7.59, Found: C 69.34, H 6.79, N 6.00, Cl 7.78.

EXAMPLE 13

2-[N-Methyl-N-((naphth-2-yl)-prop-2-yl)-amino-prop-3-yl]-6,7-dimethyl-1,2,3,4-tetrahydro-isoquinolin-1-one Prepared from 2-(3-chloropropyl)-6,7-dimethyl-1,2,3,4-tetrahydro-isoquinolin-1-one and N-methyl-2-(naphth-2-yl)-propylamine analogously to Example 1.

Yield: 45.9% of theory,
Melting point: 114°–116° C.
calculated: C 81.12, H 8.27, N 6.76, Found: C 80.92, H 8.06, N 6.70.

EXAMPLE 14

2-[N-Methyl-N-((naphth-2-yl)-eth-2-yl)-amino-prop-3-yl]-6,7-methylenedioxy-1,2,3,4-tetrahydro-isoquinolin-1-one hydrochloride Prepared from 2-(3-chloropropyl)-6,7-methylenedioxy-1,2,3,4-tetrahydro-isoquinolin-1-one and N-methyl-2-(naphth-2-yl)-ethylamine analogously to Example 1.

Yield: 40.7% of theory,
Melting point: 188°–190° C.
Calculated: C 69.09, H 6.24, N 6.19, Cl 7.84, Found: C 69.08, H 6.60, N 6.08, Cl 8.08.

EXAMPLE 15

2-[N-Methyl-N-((naphth-2-yl)-prop-3-yl)-amino-prop-3-yl]-6,7-dimethoxy-1,2,3,4-tetrahydro-isoquinolin-1-one hydrochloride Prepared from 2-(3-chloropropyl)-6,7-dimethoxy-1,2,3,4-tetrahydro-isoquinolin-1-one and N-methyl-3-(naphth-2-yl)-propylamine analogously to Example 1.

Yield: 26% of theory,
Melting point: 76°–78° C.
Calculated: C 69.62, H 7.30, N 5.80, Cl 7.34, Found: C 69.50, H 7.18, N 5.60, Cl 7.31.

EXAMPLE 16

2-[N-Methyl-N-((naphth-2-yl)-prop-3-yl)-amino-prop-3-yl]-6,7-methylenedioxy-1,2,3,4-tetrahydro-isoquinolin-1-one hydrochloride Prepared from 2-(3-chloropropyl)-6,7-methylenedioxy-1,2,3,4-tetrahydro-isoquinolin-1-one and N-methyl-3-(naphth-2-yl)-propylamine analogously to Example 1.

Yield: 17.8% of theory,
Melting point: 74°–78° C.
Calculated: C 69.44, H 6.69, N 5.99, Cl 7.59, Found: C 69.30, H 6.69, N 5.98, Cl 7.49.

EXAMPLE 17

2-[N-Methyl-N-((naphth-2-yl)-prop-3-yl)-amino-prop-3-yl]-6,7-dimethyl-1,2,3,4-tetrahydro-isoquinolin-1-one hydrochloride Prepared from 2-(3-chloropropyl)-6,7-dimethyl-1,2,3,4-tetrahydro-isoquinolin-1-one and N-methyl-3-(naphth-2-yl)-propylamine analogously to Example 1.

Yield: 26.1% of theory,
Melting point: 148°–149° C.
Calculated: C 74.57, H 7.82, N 6.21, Cl 7.86, Found: C 74.37, H 7.64, N 6.21, Cl 7.91.

EXAMPLE 18

2-[N-Methyl-N-((5-methyl-6-methoxy-naphth-2-yl)-eth-2-yl)-amino-prop-3-yl]-6,7-methylenedioxy-1,2,3,4-tetrahydro-isoquinolin-1-one hydrochloride Prepared from 2-(3-chloropropyl)-6,7-methylenedioxy-1,2,3,4-tetrahydro-isoquinolin-1-one and N-methyl-2-(5-methyl-6-methoxy-naphth-2-yl)-ethylamine analogously to Example 1.

Yield: 27% of theory,
Melting point: 234°–236° C.
Calculated: C 67.66, H 6.69, N 5.63, Cl 7.13, Found: C 67.70, H 6.59, N 5.60, Cl 7.22.

EXAMPLE 19

2-[N-Methyl-N-((naphth-2-oxy)-but-4-yl)-amino-prop-3-yl]-6,7-methylenedioxy-isoquinolin-1-one hydrochloride Prepared from 2-(3-chloropropyl)-6,7-methylenedioxy-1,2,3,4-tetrahydro-isoquinolin-1-one and N-methyl-4-(naphth-2-oxy)-butylamine analogously to Example 1.

Yield: 31% of theory,
Melting point: 157°–160° C.
Calculated: C 67.66, H 6.69, N 5.63, Cl 7.13, Found: C 67.60, H 6.67, N 5.63, Cl 7.33.

EXAMPLE 20

2-[N-Methyl-N-((6-methoxy-naphth-2-yl)-eth-2-yl)-amino-prop-3-yl]-6,7-dimethyl-1,2,3,4-tetrahydro-isoquinolin-1-one hydrochloride Prepared from 2-(3-chloropropyl)-6,7-dimethyl-1,2,3,4-tetrahydro-isoquinolin-1-one and N-methyl-2-(6-methoxy-naphth-2-yl)-ethylamine analogously to Example 1.

Yield: 28.4% of theory,
Melting point: 212°–214° C.
Calculated: C 72.01, H 7.55, N 6.00, Cl 7.59, Found: C 71.80, H 7.40, N 5.96, Cl 7.64.

EXAMPLE 21

2-[N-Methyl-N-((2-methyl-naphth-1-yl)-methyl)-amino-prop-3-yl]-6,7-dimethyl-1,2,3,4-tetrahydro-isoquinolin-1-one hydrochloride Prepared from 2-(3-chloropropyl)-6,7-dimethyl-1,2,3,4-tetrahydro-isoquinolin-1-one and N-methyl-(2-methyl-naphth-1-yl)-methylamine analogously to Example 1.

Yield: 39.4% of theory,
Melting point: 205°–206° C.
Calculated: C 74.21, H 7.61, N 6.41, Cl 8.11, Found: C 73.98, H 7.47, N 6.26, Cl 8.34.

EXAMPLE 22

3-[N-Methyl-N-((6-methoxy-5-methyl-naphth-2-yl)-eth-2-yl)-amino-prop-3-yl]-7,8-dimethoxy-1,3,4,5-tetrahydro-2H]-benzazepin-2-one Prepared from !3-(N-methylamino)-prop-3-yl]-7,8-dimethoxy-1,3,4,5-tetrahydro-2H-3-benzazepin-2-one and 2-(2-bromoethyl)-6-methoxy-5-methyl-naphthalene analogously to Example 4.

Yield: 44.7% of theory,
Melting point: 88°–92° C.
Calculated: C 73.44, H 7.81, N 5.71, Found: C 73.32, H 7.62, N 5.58.

EXAMPLE 23

3-[N-Methyl-N-((2-methyl-naphth-1-yl)-methyl)-amino-prop-3-yl]-7,8-dimethoxy-1,3,4,5-tetrahydro-2H]-benzazepin-2-one Prepared from 3-(N-methylamino)-prop-3-yl]-7,8-dimethoxy-1,3,4,5-tetrahydro-2H-3-benzazepin-2-one and 1-chloro-methyl-2-methyl-naphthalene analogously to Example 4.

Yield: 80.4% of theory,
Melting point: 114°–116° C.
Calculated: C 75.31, H 7.67, N 6.27, Found: C 75.15, H 7.65, N 6.06.

EXAMPLE 24

3-[N-Methyl-N-((2-naphth-1-yl)-eth-2-yl)-amino-prop-3-yl]-7,8-dimethoxy-1,3,4,5-tetrahydro-2H-benzazepin-2-one dihydrochloride Prepared from 3-(3-chloropropyl)-7,8-dimethoxy-1,3,4,5-tetrahydro-2H-3-benzazepin-2-one and 2-(N-methylamino)-(1-naphthyl)-ethane analogously to Example 1.

Yield: 11.3% of theory,
Melting point: 151°–155° C.
Calculated: C 66.79, H 7.20, N 5.56, Cl 14.08, Found: C 66.62, H 7.12, N 5.29, Cl 13.80.

EXAMPLE 25

3-[N-Methyl-N-((naphth-1-yl)-prop-2-yl)-amino-prop-3-yl]-7,8-dimethoxy-1,3,4,5-tetrahydro-2H-3-benzazepin-2-one hydrochloride Prepared from 3-(3-chloropropyl)-7,8-dimethoxy-1,3,4,5-tetrahydro-2H-3-benzazepin-2-one and 1-(N-methylamino)-2-(1-naphthyl)-propane analogously to Example 1.

Yield: 21.7% of theory,
Melting point: 138° C. (sintering from 108° C.).
Calculated: C 70.70, H 7.50, N 5.64, Cl 7.13, Found: C 70.45, H 7.42, N 5.39, Cl 7.38.

EXAMPLE 26

3-[N-Methyl-N-((naphth-2-oxy)-but-4-yl)-amino-prop-3-yl]-7,8-dimethoxy-1,3,4,5-tetrahydro-2H-3-benzazepin-2-one hyrochloride Prepared from 3-(3-chloropropyl)-7,8-dimethoxy-1,3,4,5-tetrahydro-2H-3-benzazepin-2-one and 1-(N-methylamino)-4-(2-naphthoxy)-butane analogously to Example 1.

Yield: 25.5% of theory,
Melting point: 210°–212° C.
Calculated: C 68.36, H 7.46, N 5.31, Cl 6.73, Found: C 68.39, H 7.37, N 5.30, Cl 6.59.

EXAMPLE 27

3-[N-Methyl-N-((2-methyl-naphth-1-yl)-eth-2-yl)-amino-prop-3-yl]-7,8-dimethoxy-1,3,4,5-tetrahydro-2H-3-benzazepin-2-one hydrochloride Prepared from 3-(3-chloropropyl)-7,8-dimethoxy-1,3,4,5-tetrahydro-2H-3-benzazepin-2-one and 1-(N-methylamino)-2-(2-methyl-naphth-1-yl)-ethane analogously to Example 1.

Yield: 34.8% of theory,
Melting point: 217°–219° C.
Calculated: C 70.07, H 7.50, N 5.64, Cl 7.13, Found: C 69.91, H 7.45, N 5.75, Cl 7.29.

EXAMPLE 28

3-[N-Methyl-N-((naphth-1-yl)-eth-2-yl)-amino-prop-3-yl]-7,8-dimethoxy-1,3-dihydro-2H-3 -benzazepine Prepared from 3-[N-methyl-N-((naphth-1-yl)-eth-2-yl)-amino-prop-3-yl]-7,8-dimethoxy-1,3-dihydro-2H-3-benzazepin-2-one and lithium aluminium hydride analogously to Example 8.

Yield: 44.6% of theory,
Melting point: oil.
Calculated: C 78.10, H 7.96, N 6.51, Found: C 78.31, H 7.96, N 6.50.

EXAMPLE 29

3-[N-Methyl-N-((naphth-1-yl)-eth-2-yl)-amino-prop-3-yl]-7,8-dimethoxy-1,3,4,5-tetrahydro-2H-3-benzazepin-1,2-dione hydrochloride Prepared from 3-(3-chloropropyl)-7,8-dimethoxy-1,3,4,5-tetrahydro-2H-3-benzazepin-1,2-dione and 1-(N-methyl-amino)-2-(1-naphthyl)-ethane analogously to Example 1.

Yield: 13.9% of theory,
Melting point: 244°–246° C.
Calculated: C 67.65, H 6.69, N 5.64, Cl 7.13, Found: C 67.55, H 6.49, N 5.81, Cl 7.18.

EXAMPLE 30

3-[N-Methyl-N-((naphth-1-yl)-eth-2-yl)-amino-prop-3-yl]-7,8-dimethoxy-1-hydroxy-1,3,4,5-tetrahydro-2H-3-benzazepin-2-one hydrochloride Prepared from 3-(3-chloropropyl)-7,8-dimethoxy-1-hydroxy-1,3,4,5-tetrahydro-2H-3-benzazepin-2-one and 1-(N-methyl-amino)-2-(1-naphthyl)-ethane analogously to Example 1.

Yield: 43.3% of theory,
Melting point: 155°–159° C.
Calculated: C 67.66, H 6.69, N 5.64, Cl 7.13, Found: C 67.58, H 6.86, N 5.46, Cl 7.44.

EXAMPLE 31

2-[N-Methyl-N-((naphth-2-yl)-methyl)-amino-prop-3-yl]-5,6-dimethoxy-phthalimidine Prepared from 2-[N-methyl-N-(naphth-2-yl)-methyl-amino-prop-3-yl]-5,6-dimethoxy-phthalimide and zinc/glacial acetic acid analogously to Example 10.

Yield: 43% of theory,
Calculated: C 62.89, H 6.33, N 5.87, Cl 14.85, Found: C 63.00, H 6.54, N 6.02, Cl 14.68.

$R_f$ value: 0.45 (silica gel, methylene chloride/methanol=9:1).

EXAMPLE 32

2-[N-Methyl-N-((naphth-2-yl-oxy)-but-4-yl)-amino-prop-3-yl]-5,6-dimethoxy-phthalimidine Prepared from 2-[N-methyl-N-((naphth-2-yl-oxy)-but-4-yl)-amino-prop-3-yl]-5,6-dimethoxy-phthalimide and zinc/glacial acetic acid analogously to Example 10.

Yield: 12% of theory,
Calculated: C 63.04, H 6.42, Cl 13.29, Found: C 62.98, H 6.34, Cl 13.73.

$R_f$ value: 0.29 (silica gel, methylene chloride/methanol=9/1).

EXAMPLE 33

2-[N-Methyl-N-((naphth-1-yl)-eth-2-yl)-amino-prop-3-yl]-5,6-dimethoxy-phthalimidine Prepared from 2-[N-methyl-N-((naphth-1-yl)-eth-2-yl)-amino-prop-3-yl]-5,6-dimethoxy-phthalimide and zinc/glacial acetic acid analogously to Example 10.

Yield: 58% of theory,
Calculated: C 68.63, H 6.87 N 6.16, Cl 7.79; Found: C 68.72, H 7.04, N 6.10, Cl 7.93.

$R_f$ value: 0.32 (silica gel, methylene chloride/methanol=9/1).

EXAMPLE 34

2-[N-Methyl-N-((5-methyl-6-methoxy-naphth-2-yl)-eth-2-yl)-amino-prop-3-yl]-5,6-dimethoxy-phthalimidine Prepared from 2-[N-methyl-N-((5-methyl-6-methoxy-naphth-2-yl)-eth-2-yl)-amino-prop-3-yl]-5,6-dimethoxy-phthalimide and zinc/glacial acetic acid analogously to Example 10.

Yield: 74% of theory,
Calculated: C 67.39, H 7.07, N 5.61, Cl 7.10, Found: C 67.47, H 7.15, N 5.30, Cl 7.55.
$R_f$ value: 0.26 (silica gel, methylene chloride/methanol=9/1).

EXAMPLE 35

2-[N-Methyl-N-((2-methyl-naphth-1-yl)-methyl)-amino-prop-3-yl]-5,6-dimethoxy-phthalimidine Prepared from 2-[N-methyl-N-((2-methyl-naphth-1-yl)-methyl)-amino-prop-3-yl]-5,6-dimethoxy-phthalimide and zinc/glacial acetic acid analogously to Example 10.

Yield: 21% of theory,
Calculated: C 68.63, H 6.87, N 6.16, Cl 7.79, Found: C 68.45, H 6.78, N 6.48, Cl 7.77.
$R_f$ value: 0.52 (silica gel, methylene chloride/methanol=9/1).

EXAMPLE 36

3-[N-Methyl-N-((naphth-2-yl)-eth-2-yl)-amino-prop-3-yl]-7,8-dimethoxy-1,3,4,5-tetrahydro-2H-3-benzazepin-2-one hyrochloride Prepared from 3-(3-chloropropyl)-7,8-dimethoxy-1,3,4,5-tetrahydro-2H-3-benzazepin-2-one and 2-(2-methylamino-ethyl)-naphthalene analogously to Example 1.

Yield: 23% of theory,
Melting point: 215°-216° C.
Calculated: C 69.62, H 7.30, N 5.80, Cl 7.34, Found: C 69.43, H 7.45, N 5.63, Cl 7.96.

EXAMPLE 37

2-[N-Methyl-N-((5-methyl-6-methoxy-naphth-2-yl)-eth-2-yl)-amino-prop-3-yl]-6,7-dimethoxy-1,2,3,4-tetrahydro-isoquinoline dihydrochloride Prepared from 2-[N-methyl-N-((5-methyl-6-methoxy-naphth-2-yl)-eth-2-yl)-amino-prop-3-yl]-6,7-dimethoxy-1,2,3,4-tetrahydro-isoquinolin-1-one and lithium aluminium hydride in tetrahydrofuran/ether analogously to Example 8.

Yield: 87.8% of theory,
Melting point: 254°-256° C.
Calculated: C 65.05, H 7.52, N 5.23, Found: C 65.11, H 7.76, N 5.32.

EXAMPLE 38

2-[N-Methyl-N-((2-methyl-naphth-1-yl)-methyl)-amino-prop-3-yl]-6,7-dimethoxy-1,2,3,4-tetrahydro-isoquinoline dihydrochloride Prepared from 2-[N-methyl-N-((2-methyl-naphth-1-yl)-methyl)-amino-prop-3-yl]-6,7-dimethoxy-1,2,3,4-tetra-hydro-isoquinolin-1-one and lithium aluminium hydride in tetrahydrofuran/ether analogously to Example 8.

Yield: 71.7% of theory,
Melting point: 218°-220° C.
Calculated: C 65.81, H 7.78, N 5.70, Found: C 66.07, H 7.45, N 5.70.

EXAMPLE 39

2-[N-Methyl-N-((naphth-2-oxy)-but-4-yl)-amino-prop-3-yl]-6,7-dimethoxy-1,2,3,4-tetrahydro-isoquinoline dihydrochloride Prepared from 2-[N-methyl-N-((naphth-2-oxy)-but-4-yl)-amino-prop-3-yl]-6,7-dimethoxy-1,2,3,4-tetrahydro-isoquinolin-1-one and lithium aluminium hydride in tetrahydrofuran/ether analogously to Example 8.

Yield: 75% of theory,
Melting point: 247°-249° C.
Calculated: C 65.03, H 7.52, N 5.23, Found: C 65.36, H 7.28, N 4.97.

EXAMPLE I

Tablets containing 7.5 mg of 3-[N-methyl-N-((6-methoxy-naphth-yl)-eth-2-yl)-amino-prop-3-yl]-7,8-dimethoxy-1,3,4,5-tetrahydro-2H-3-benzazepin-2-one

| Composition: | |
|---|---|
| 1 tablet contains: | |
| Active substance | 7.5 mg |
| Corn starch | 59.5 mg |
| Lactose | 48.0 mg |
| Polyvinylpyrrolidone | 4.0 mg |
| Magnesium stearate | 1.0 mg |
| | 120.0 mg |

Method of preparation

The active substance, corn starch, lactose and polyvinylpyrrolidone are mixed together and moistened with water. The moist mixture is pressed through a screen with a mesh size of 1.5 mm and dried at about 45° C. The dry granulate is passed through a screen with a mesh size of 1.0 mm and mixed with magnesium stearate. The finished mixture is compressed in a tablet press using punches 7 mm in diameter which are provided with a dividing notch to form tablets. Weight of tablet: 120 mg

EXAMPLE II

Coated tablets containing 5 mg of 3-[N-methyl-N-((6-methoxy-naphth-2-yl)-eth-2-yl)-amino-prop-3-yl]-7,8-dimethoxy-1,3,4,5-tetrahydro-2H-3-benzazepin-2-one

| 1 tablet core contains: | |
|---|---|
| Active substance | 5.0 mg |
| Corn starch | 41.5 mg |
| Lactose | 30.0 mg |
| Polyvinylpyrrolidone | 3.0 mg |
| Magnesium stearate | 0.5 mg |
| | 80.0 mg |

Method of preparation

The active substance, corn starch, lactose and polyvinylpyrrolidone are thoroughly mixed and moistened with water. The moist mass is pressed through a screen with a mesh size of 1 mm, dried at about 45° C. and then the granules are passed through the same screen again. After the addition of magnesium stearate, convex tablet cores with a diameter of 6 mm are compressed in a tablet making machine. The tablet cores thus produced are coated in known manner with a coating consisting essentially of sugar and talc. The finished coated tablets are polished with wax. Weight of coated tablet: 130 mg

EXAMPLE III

Ampoules containing 5 mg of 3-[N-methyl-N-((6-methoxy-naphth-2-yl)-eth-2-yl)-amino-prop-3-yl]-7,8-dimethoxy-1,3,4,5-tetrahydro-2H-3-benzazepin-2-one

| 1 ampoule contains: | |
|---|---|
| Active substance | 5.0 mg |
| Sorbitol | 50.0 mg |
| Water for injections ad | 2.0 mg |

Method of preparation

In a suitable container, the active substance is dissolved in water for injections and the solution is made isotonic with sorbitol.

After filtration through a membrane filter the solution is transferred into cleaned and sterilised ampoules under a current of $N_2$ and autoclaved for 20 minutes in a steam current.

EXAMPLE IV

Suppositories containing 10 mg of 3-[N-methyl-N-((6-methoxy-naphth-2-yl)-eth-2-yl)-amino-prop-3-yl]-7,8-dimethoxy-1,3,4,5-tetrahydro-2H-3-benzazepin-2-one

| 1 suppository contains: | |
|---|---|
| Active substance | 0.010 g |
| Hard fat (e.g. Witepsol H 19 and W 45) | 1.690 g |
| | 1.700 g |

Method of preparation

The hard fat is melted. At 38° C. the ground active substance is homogeneously dispersed in the melt. It is cooled to 35° C. and poured into slightly chilled suppository moulds.

EXAMPLE V

Drops solution containing 10 mg of 3-[N-methyl-N-((6-methoxy-naphth-2-yl)-eth-2-yl)-amino-prop-3-yl]-7,8-dimethoxy-1,3,4,5-tetrahydro-2H-3-benzazepin-2-one

| 100 ml of solution contain: | |
|---|---|
| Active substance | 0.2 g |
| Hydroxyethylcellulose | 0.15 g |
| Tartaric acid | 0.1 g |
| Sorbitol solution containing 70% dry matter | 30.0 g |
| Glycerol | 10.0 g |
| Benzoic acid | 0.15 g |
| Distilled water ad | 100 ml |

Method of preparation

Distilled water is heated to 70° C. Hydroxyethylcellulose, benzoic acid and tartaric acid are dissolved therein with stirring. The solution is cooled to ambient temperature and the glycerol and sorbitol solution are added with stirring. At ambient temperature the active substance is added and stirred until fully dissolved. The solution is then evacuated with stirring in order to remove any air from the liquid.

What is claimed is:

1. A compound of the formula

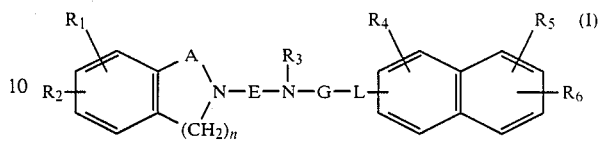

wherein:

n represents the number 1 or 2,

A represents a $-CH_2-$, $-CO-$, $-CH_2CH_2-$, $-CH=CH-$, $-CH_2CO-$, $-CH_2CS-$, $-COCO-$ or
  x            x $-CHOH-CO-$ group,
  x wherein the atom marked with an x is linked to the phenyl nucleus, E represents a straight chained alkylene group with 2 to 4 carbon atoms optionally substituted by an alkyl group with 1 to 3 carbon atoms, G represents a straight chained alkylene group with 1 to 5 carbon atoms optionally substituted by an alkyl group with 1 to 3 carbon atoms, L represents a bond or an oxygen atom, if G represents a straight chained alkylene group with 2 to 5 carbon atoms optionally substituted by an alkyl group with 1 to 3 carbon atoms, or a bond $R_1$ and $R_2$, which may be identical or different, represent alkyl or alkoxy groups each having 1 to 3 carbon atoms in each alkyl moiety or $R_1$ and $R_2$ together represent an alkylenedioxy group with 1 or 2 carbon atoms, $R_3$ represents a hydrogen atom, an alkyl group with 1 to 3 carbon atoms or an allyl group, and $R_4$, $R_5$ and $R_6$, which may be identical or different, represent hydrogen atoms, alkyl or alkoxy groups each having 1 to 3 carbon atoms in each alkyl moiety, or a pharmaceutically acceptable salt thereof.

2. A compound of formula I, as claimed in claim 1, wherein:

A, L and n are defined as in claim 1,

E represents an ethylene or n-propylene group,

G represents a straight chained alkylene group with 1 to 4 carbon atoms optionally substituted by a methyl group, $R_1$ represents a methyl or methoxy group, $R_2$ represents a methyl or methoxy group or $R_1$ and $R_2$ together represent a methylenedioxy group, $R_3$ represents a methyl group, $R_4$ represents a hydrogen atom or a methyl group, $R_5$ represents a hydrogen atom, or a methyl or methoxy group, and $R_6$ represents a hydrogen atom or a methoxy group, or a pharmaceutically acceptable salt thereof.

3. A compound of formula I as claimed in claim 1, wherein:

n represents the number 1 or 2,

A represents a —CH₂—, —CO— or —CH₂CO— group,

E represents an n-propylene group,

G represents an ethylene group,

L represents a bond, $R_1$ and $R_2$ each represent a methoxy group or together represent a methylenedioxy group, $R_3$ represents a methyl group, $R_4$ represents a hydrogen atom, $R_5$ represents a hydrogen atom, or a methyl or methoxy group, and $R_6$ represents a hydrogen atom or a methoxy group, or a pharmaceutically acceptable salt thereof.

4. 3-[N-Methyl-N-((6-methoxy-naphth-2-yl)-eth-2-yl)-amino-prop-3-yl]-7,8-dimethoxy-1,3,4,5-tetrahydro-2H-3-benzazepin-2-one or a pharmaceutically acceptable salt thereof.

5. 3-[N-Methyl-N-((6-methoxy-5-methyl-naphth-2-yl)-eth-2-yl)-amino-prop-3-yl]-7,8-dimethoxy-1,3,4,5-tetrahydro-2H]-benzazepin-2-one or a pharmaceutically acceptable salt thereof.

6. A pharmaceutical composition suitable for treating sinus tachycardia and ischemic heart disease which comprises a therapeutic amount of a compound of formula I, as set forth in claim 1, together with one or more inert carriers or diluents.

7. A method for treating sinus tachycardia or ischaemic heart disease which comprises administering to a patient suffering from the same a therapeutic amount of a compound of formula I, as claimed in claims 1, 2, 3, 4, or 5.

* * * * *